(12) United States Patent
Potter et al.

(10) Patent No.: US 8,140,268 B2
(45) Date of Patent: Mar. 20, 2012

(54) COMPUTATIONAL METHOD FOR DRUG DISCOVERY AND RECEPTOR DESIGN

(75) Inventors: Michael Jason Potter, North Potomac, MD (US); Hillary Sue Rodman Gilson, North Potomac, MD (US); Michael Kenneth Gilson, North Potomac, MD (US)

(73) Assignee: VeraChem, LLC, Germantown, MD (US)

( * ) Notice: Subject to any disclaimer, the term of this patent is extended or adjusted under 35 U.S.C. 154(b) by 1185 days.

(21) Appl. No.: 11/695,494

(22) Filed: Apr. 2, 2007

(65) Prior Publication Data
US 2009/0326878 A1    Dec. 31, 2009

Related U.S. Application Data

(60) Provisional application No. 60/787,522, filed on Mar. 31, 2006.

(51) Int. Cl.
*G01N 33/48* (2006.01)
*G06G 7/58* (2006.01)
(52) U.S. Cl. .............................. 702/19; 703/11; 435/7.1
(58) Field of Classification Search .................. None
See application file for complete search history.

(56) References Cited

OTHER PUBLICATIONS

N. Nakajima et al. Chemical Physics Letters 278 (1997) 297-301.*
Mendieta et al. Proteins: Structure, Function, and Bioinformatics,2001, vol. 44, Issue 4, pp. 460-469.*
Prusis et al. Journal of Molecular Graphics and Modelling, vol. 15, Issue 5, 1997, pp. 307-317.*
Chen et al. Biophysical Journal, vol. 87, Issue 5, Nov. 2004, pp. 3035-3049.*
Kolossvary et al. J. Phys. Chem. A, 1997, 101, 9900-9905.*
Luo et al. J. Am. Chem. Soc. 2000, 122, 2934-2937.*
Alberts, et al. (1994) *Molecular Biology of the Cell* [3$^{rd}$ Ed.] Chapter 5: Protein Function, pp. 195-222.
Chen, et al. (2010) "Modeling Protein—Ligand Binding by Mining Minima." *J. Chem. Theory Comput.* 6: 3540-3557.
Mathews & van Holde (1996) *Biochemistry* Chapter 6: "The Three-Dimensional Structure of Proteins", pp. 165-213.

* cited by examiner

*Primary Examiner* — Michael Borin
(74) *Attorney, Agent, or Firm* — Hunton & Williams LLP

(57) ABSTRACT

The present invention provides a method of predicting the mutual affinity of two molecules for each other in solution, by computing the configuration integrals of the free molecules and their bound complex as sums over local energy wells. The invention makes accurate calculations computationally tractable for a range of molecular systems by several means, including restraining the conformations of selected molecular components, and using a single conformation representative of an energy well to correct an efficient but less accurate energy model toward a slower but more accurate model.

45 Claims, 4 Drawing Sheets

COMPUTATIONAL METHOD FOR DRUG DISCOVERY AND RECEPTOR DESIGN

CROSS-REFERENCE TO RELATED APPLICATIONS

This Application claims benefit of priority to U.S. Provisional Application 60/787,522 filed Mar. 31, 2006.

STATEMENT REGARDING FEDERALLY SPONSORED RESEARCH OR DEVELOPMENT

This invention was made with government support under grant 4R44GM075350, "Software for Accurate Ligand-Protein Affinities" awarded by the NIH. The United States government has certain rights in the invention.

BACKGROUND OF THE INVENTION

General Background

In the fields of biomedicine and chemistry, many useful molecules gain their utility from their ability to tightly bind specific other molecules, for example:

1 Pharmaceutical Industry
   1.1 Penicillin is a molecule that kills harmful bacteria by binding and inhibiting proteins which the bacteria require for survival. The proteins are enzymes which normally would construct the bacterial cell wall by chemically linking small chemical units into larger ones that form the cell wall.
   1.2 One of the most important treatments for HIV/AIDS is a protease inhibitor, a molecule that specifically binds enzymes belonging to the AIDS virus and prevents them from carrying out their normal function. See, for example, U.S. Pat. No. 6,071,916.
   1.3 Among the most valuable and widely used medications today are molecules that prevent heart attacks by preventing the human body from synthesizing cholesterol. See, for example, U.S. Pat. No. 6,180,660. These molecules include Pfizer's drug atorvastatin (Lipitor®) and Merck's drug simvastatin (Zocor®). These molecules bind and inhibit a protein known as HMG-CoA reductase. This protein is an enzyme that is involved in the synthesis of cholesterol.
   1.4 Sometimes a molecule with the potential to be used as a valuable medication, such as one of the examples above, is chemically unstable or has other problems that make it difficult to prepare, store or administer. One way to solve these problems is to mix the drug molecule with another molecule, known as a carrier, which binds it and thereby improves its properties as a therapeutic agent. See, for example, U.S. Pat. No. 4,596,795.

2 Chemical Industry
   2.1 Much work in the chemical industries involves converting one type of molecule to another type of molecule. For example, huge chemical plants convert petroleum into plastics, pigments, detergents, etc. Forcing these conversions to occur often requires very hot temperatures, strong acids, etc. However, a few conversions can be carried out at room temperature without harsh chemicals by using enzymes, which work by binding the molecules to be converted and thereby catalyzing their chemical conversion. Such "green chemistry" saves energy and produces less pollution. Enzymes that bind and act upon specific targeted molecules also are used in the production of food ingredients, such as high-fructose corn syrup. See, for example, U.S. Pat. No. 4,077,842 and references therein.
   2.2 The first steps of chemical (and pharmaceutical) production almost always yield a mixture of molecules that include the specific molecule of interest. A widely used technique for purifying the desired molecule out of this mixture is to flow the mixture over a material that has molecular parts which bind the molecule of interest and hold it back, while the undesired molecules continue to flow past.

3 Nanotechnology.
   Extremely small objects and devices hold great promise in applications such as medicine, measurement and detection, and computers, but building such small devices is very difficult. One approach under investigation is to coat two parts that need to be assembled together with molecules that bind each other. Then simply mixing the parts will lead to assembly due to the mutual attraction of the molecules with which they are coated. See, for example, U.S. Pat. No. 6,962,747.

The binding of a small molecule (typically molecular weight less than 1000 Daltons) to a macromolecule like a protein is of central importance in many of these practical applications, and many other useful applications involving binding interactions between a small molecule and a macromolecule could be mentioned. However, it is known to those skilled in the art that discovering or inventing a small molecule that binds a targeted protein, or alternatively modifying a protein so that it binds a targeted small molecule, are difficult challenges. Success in such endeavors is not achieved by a reliable, stepwise process of molecular design, but instead requires a large component of trial and error.

Over recent decades, computer models have begun to play a role in the design of molecules intended to bind a specific protein and thus to be useful as medications, as in examples 1.1-1.3 above. Such computer models aim to predict whether a given molecule will bind the targeted protein and, if so, how tightly it will bind. If such a model were accurate, then it could be used to test a proposed molecule computationally, rather than experimentally, and thereby save the time and money required to procure or synthesize various molecules and test them experimentally.

Unfortunately, existing computer models suffer from one or both of two major problems. First, these models are notoriously unreliable and inaccurate. See, for example Warren et al, A Critical Assessment of Docking Programs and Scoring Functions, J Med Chem, 2006, 49, 5912-5931. As a consequence, they do not avoid the requirement for extensive experimental work in order to arrive at a molecule that binds the targeted protein tightly enough to have potential as a medication. Second, those computer models which are considered to be most accurate are so complex and demanding computationally that they require weeks or more of computer time and are therefore impractical for most real-world projects. For example, a recent research dissertation reported using 20 fast computers for a week to make a prediction for a single molecule and protein (http://www.columbia.edu/~mrs2144/MRSdissert.pdf).

The current state of the art can be explained by scenarios common in early-stage drug discovery. In one important early stage of drug-discovery, the research team knows that a specific protein plays a role in a disease, and the team seeks a molecule that will bind and inhibit the protein's function in order to treat the disease. A widely used initial approach to discover such a molecule is to employ a computer modeling technique in order to computationally screen a long list of available molecules that could be purchased and studied. This computational screening process often begins with the detailed three-dimensional structure of the targeted protein. This structure may have been obtained by X-ray crystallography or other experimental or computational methods. A computer model is used to spatially fit each candidate molecule into a binding site of the targeted protein, and then to use the fitted structure to assess the likelihood that each molecule will in fact bind the protein. The molecules are then ranked according to the likelihood that they will bind the targeted protein, and molecules at the top of the list are procured and tested experimentally. The list of available molecules may stretch into the millions, so a fast computer model is required. However, it is known that the computer models used at this stage of the project are not accurate enough to ensure that the top-ranked molecules will in reality bind the targeted protein, so many of the experimental tests do not yield positive results. Conversely, existing computer models often assign poor ranks to molecules which in fact bind the target tightly, and thus can lead the research team to miss molecules that would have been useful for the project. These considerations highlight the need for a more accurate computer model that can rapidly predict whether an available compound will bind a targeted protein.

In another important stage of drug-discovery, the research team has already identified a molecule, known as a lead compound, that binds the targeted protein, but not as tightly as is required for a drug. This lead compound may have been obtained by the screening process described in the previous paragraph, or by some other method. The next stage of the project, called lead optimization, constitutes an effort to devise a chemical variant of the lead compound that binds the targeted protein with high enough affinity to be potentially useful as a drug. Chemical variants of the lead compound are proposed, custom-synthesized by medicinal chemists, and tested for affinity to the protein. This stage is time-consuming and costly because of the challenge of chemically synthesizing each variant of the lead compound. The time required to work through this stage is especially costly because delays postpone the date at which the company will see revenues from the new drug, as well as the date when patients suffering from the disease will be able to use the new therapy. In addition, drug companies compete with each other and there is great value in arriving at a new medication before the competition. Unfortunately, even the most highly regarded computer models rarely provide medicinal chemists with accurate and timely guidance regarding what variants of the lead compound will bind with highest affinity, as is known to those skilled in the art.

These scenarios of early stage drug-discovery highlight the critical need for a more accurate computer model to predict how tightly a proposed variant of a lead compound will bind a targeted protein. Such a model will reduce costs and thus speed the discovery of new drugs important to the pharmaceutical industry and to people requiring treatment.

As discussed above, there are many other uses for a computer model of binding in addition to drug-discovery. The shortcomings of existing computer models, just discussed in the context of drug-discovery, have equally negative consequences in these other areas of application. For example, the inaccuracy of computer models of binding makes it difficult and expensive to modify the binding site of an existing enzyme so that it will bind and act upon a different chemical substrate. This makes it difficult to arrive at enzymes useful to the chemical and food industries.

Technical Background

The binding affinity of two molecules, receptor R and ligand L forming complex RL, is specified by a binding constant $K_b$, or a dissociation constant $K_d$, defined by:

$$K_b = K_d^{-1} \equiv \left(\frac{C_{RL}C^o}{C_R C_L}\right)_{equilibrium} \qquad \text{Equation 1}$$

where $C_R$, $C_L$ and $C_{RL}$ are the concentrations of molecule R, molecule L and their complex RL, respectively, $C^o$ is the standard concentration (typically 1 mole per liter (M)) and the quantity in parentheses is the ratio of concentrations at equilibrium, typically in units of moles per liter (M). The standard binding free energy $\Delta G^o$ can then be written as $$\Delta G^o = -R_g T \ln(K_b) \qquad \text{Equation 2}$$

where $R_g$ is the gas constant and T is absolute temperature. The more negative this quantity, the greater the binding affinity of molecules R and L for each other. The central challenge in the present field is to compute the standard free energy of two specified molecules for each other.

In order to understand the principles underlying any method of computing $\Delta G^o$, it is important to be aware that small molecules and proteins are all flexible to some degree at least, so they can adopt various three dimensional configurations or conformations. Their motions are governed by various interatomic forces, such as the forces of covalent bonding, van der Waals interactions, electrostatic interactions, hydrogen bonds, etc. If a molecule is immersed in a solvent, such as water or chloroform, then the solvent exerts additional forces on the molecule. For example, water tends to pull apart charged atoms, and drive together nonpolar atoms. The various forces that act upon a molecule determine what conformations it tends to adopt. More specifically, statistical thermodynamics states that the forces experienced by a molecule tend to drive it into conformations of low energy, where the energy is defined as the molecule's own potential energy U plus an additional solvation energy contribution W from the solvent in which it is immersed. Similarly, molecules tend to bind each other if they can form a complex of low energy, relative to the energies they possess when they are not bound to each other.

Mathematically, the conformation of a molecule or complex can be specified by a set of atomic coordinates symbolized as a vector or a sequence of vectors r. By way of non-limiting example, when Cartesian coordinates are used, $r=(x_k, y_k, z_k)$ where $k \leq 3N_{atoms}-6$ and $N_{atoms}$ is the number of atoms in the molecule. A sequence of conformations i may be represented by $(r_i)$, where each $r_i$ is a conformation. Potential and solvation energies can then be written as functions of r, respectively U(r) and W(r). A molecule or a complex is stable to the extent that it has many conformations where U(r)+W(r) is low. The standard free energy of binding can be written as $$\Delta G^o = -R_g T \ln\left(\frac{C^o}{8\pi^2} \frac{Z_{RL}}{Z_R Z_L}\right) \qquad \text{Equation 3}$$

where $C^o$ is the standard concentration (normally 1 M) and the quantities Z are configuration integrals for the subscripted complex RL and the separate molecules R and L:

$$Z \equiv \int_{-\infty}^{\infty} e^{-(U(r)+W(r))R_gT} dr \qquad \text{Equation 4}$$

These formulae indicate that the more low-energy conformations the complex RL can adopt relative to the unbound molecules R and L, the greater will be their binding affinity. The equations presented above provide the theoretical underpinnings of most or all of the computational models of binding in use today, either explicitly or implicitly.

These equations also can be used to explain why it is difficult to devise an accurate method of computing the standard free energy of binding. One challenge has been to simply arrive at equations suitable for computing the standard free energy of binding. A number of computational methods have proven to be based upon erroneous or incomplete theoretical foundations.

A second challenge has been to develop a method of computing the potential energy of a molecule as a function of conformation; i.e., to compute U(r). One approach is to rely upon first principles quantum mechanical methods which account in detail for the electronic structure of a molecule or complex. (See, for example, the use of such methods in U.S. Pat. No. 6,106,562.) However, first principles quantum mechanical calculations are too slow to allow energies to be computed for the many molecular conformations required to evaluate the configuration integrals Z with useful accuracy. A second approach is to use what are known as empirical force fields. (See, for example, U.S. Pat. No. 6,785,665, which describes a method of constructing such a force field, and U.S. Pat. No. 5,424,963 for a previous application of the empirical force field associated with the AMBER computer program.) Empirical force fields are approximations, so they are not perfectly accurate.

A third challenge has been to arrive at a method of computing the solvation energy as a function of molecular conformation W(r). An important early approach was to carry out computer simulations in which many water molecules, often thousands of them, were treated explicitly, surrounding the molecules of interest and vibrating and diffusing due to heat energy. However, this approach is highly time-consuming. More recently, it has been discovered that the solvation energy can be computed to useful accuracy by what are called implicit solvent models. These avoid explicitly modeling many water molecules, and instead estimate the solvation energy via simpler and computationally faster physical models. The most widely accepted class of implicit solvent models treat the solvent as a high-dielectric medium that follows the laws of classical electrostatics. Within this approach, the most accurate methods solve the classical electrostatic equations (i.e., the Poisson-Boltzmann equation) via numerical methods such as the method of finite differences. These numerical methods provide a good estimate of the electrostatic part of the solvation energy of a molecule in a given conformation within typically seconds to a few minutes of computer time. This makes them much faster than explicit solvent models, but they are still too slow for some applications. A more rapid electrostatic approximation is the generalized Born approximation. (See, for example, J. Comput.-Aided Molec. Design 5:5-20, 1991 and U.S. Pat. No. 5,420,805.) The generalized Born approximation is considerably faster, but is widely regarded by those skilled in the art as being significantly less accurate than numerical solutions of the Poisson-Boltzmann equation. In addition to the electrostatic part just discussed, the salvation energy also includes a nonpolar part which is often approximated as proportional to molecular surface area, with an empirically derived coefficient.

A fourth challenge in the calculation of binding affinities is evaluation of the ratio of configuration integrals found in Equation 3 and defined in Equation 4. In one general approach, computer simulations are used to compute the thermodynamic work of bringing the two molecules together to form a bound complex. This approach can be accurate, but is notoriously time-consuming computationally, primarily because the simulations must sample a very large number of molecular conformations during the binding process, and simulations typically sample conformations essentially randomly. On the other hand, less rigorous approaches have not yielded accurate results. A new class of approaches which began to emerge in the late 1990s sought to achieve the rigor of the simulation methods while achieving much greater computational speed (Gilson, et al., Chem. Biol. 4:87-92, 1997). This approach, here termed Local Integration, uses the fact that the largest contributions to a configuration integral come from low-energy conformations of the molecule or complex, because that is where the integrand is largest (Equation 4). The configuration integral thus can be approximated as a sum of local contributions from local energy wells:

$$Z \approx \sum_{i=1}^{M} Z_i \equiv \sum_{i=1}^{M} \int_{J_{i=1}} e^{-(U(r)+W(r))/R_gT} dr \qquad \text{Equation 5}$$

Here i indexes M energy wells and $Z_i$ is a configuration integral local to energy well i, as indicated by the subscript i on the integral sign. Methods in this class can take advantage of powerful optimization algorithms to discover low-energy conformations i much more rapidly than is possible in the course of a simulation. However, the methods in this class vary significantly in how they evaluate the local configuration integrals $Z_i$.

The apparently earliest Local Integration method, Mining Minima (Head et al, J. Phys. Chem. A 101:1609-1618, 1997), evaluates a local configuration integral $Z_i$ via unbiased Monte Carlo sampling in a region with hypervolume $V_i$ in the vicinity of energy minimum i located at internal coordinates $r_i$:

$$Z_i \approx V_i \frac{1}{n} \sum_{j=1}^{n} e^{-(U(r_j)+W(r_j))/R_gT} \qquad \text{Equation 6}$$

This sum runs over n conformations $r_j$ generated computationally by adding small, uniformly distributed random numbers to $r_i$, and thereby sampling conformations $r_j$ in the vicinity of $r_i$ and within hypervolume $V_i$. The range of the random numbers is gradually expanded in the course of the calculation until the value of $Z_i$ for energy well i converges to within a preselected tolerance. This method significantly advanced the state of the art, but had two important limitations. First, it could not efficiently include sampling of bond-lengths and bond-angles, but instead included only bond-torsions as degrees of freedom. Second, the calculations are excessively time-consuming for many molecular systems of interest because the number of samples n required to achieve convergence is large.

The second method in the class of Local Integration methods, MINTA (U.S. Pat. No. 6,178,384), sought to enable effective sampling over not only torsion angles but also bond-lengths and bond-angles. This was accomplished by using a parabolic (harmonic) representation of the energy in the vicinity of each energy minimum i to guide the selection of conformational samples in the energy minimum. However, this method still possesses significant drawbacks. First, it has been found (Potter & Gilson, J. Phys. Chem. A 106:563-566, 2002) to rely upon an incorrect expression for the configuration integral, different from those listed above, and therefore can yield results with significant errors. Second, it still requires a large number of conformational samples; that is, n is still large. As a consequence, the method is still too slow for many applications of interest. For example, it was reported to require 10,000 conformations per energy minimum for a small bimolecular complex (U.S. Pat. No. 6,178,384). Far more samples would be required for a protein complex with a small molecule, because even more samples would need to be generated to integrate within each energy well. Even more importantly, a protein has far too many local energy minima i to permit the minima to be discovered computationally and integrated by a current computer within an acceptable amount of time. Thousands of years or more might be required to complete such a calculation. As a consequence, this method is at best difficult and in many cases impossible to apply to many of the molecular systems for which the ability to compute binding affinities would be most valuable.

More recently, a more efficient Local Integration method has been described and shown to provide good accuracy and computational speed for binding reactions involve a small molecule and a small receptor. The method, M2 (Chang et al., J. Phys. Chem. B 107:1048-1055, 2003; Chang & Gilson, J. Am. Chem. Soc. 126:13156-13164, 2004), estimates the configuration integral $Z_i$ in a given energy well i as follows. First, the matrix of second derivatives of the energy is computed with respect to atomic coordinates expressed in terms of bond-lengths, bond-angles, and bond-torsions. This matrix is then diagonalized to yield $3N_{atoms}-6$ eigenvalues and $3N_{atoms}-6$ corresponding eigenvectors, where $N_{atoms}$ is the number of atoms in the molecule or complex. The energy in the vicinity of the energy minimum can then be approximated by forming a multidimensional Taylor series expansion and using its second order (quadratic) term to define a multidimensional parabola with principal axes lying along the eigenvectors and corresponding coefficients (or force constants) equal to the corresponding eigenvalues. (Implementations to date have not employed higher-order terms in the Taylor series expansion because this would increase the complexity of the calculations and it has not been clear that the improvement in accuracy would be substantial.) This approximation, often termed the harmonic approximation, allows the integrand of the local configuration integral to be approximated as a multidimensional Gaussian function with the same principal axes as the parabola and with corresponding standard deviations that can readily computed from the eigenvalues by formulae well known to those skilled in the art. This multidimensional Gaussian can then readily be evaluated as the sum of contributions along each principal axis (eigenvector). Typically, the integral along eigenvector j is restricted to a domain determined by the standard deviations of the Gaussian along this eigenvector and/or by a maximum allowed excursion of any torsion angle as the molecule is distorted along the eigenvector. These limits prevent the integration range from extending into any neighboring energy wells. When the integration method is based purely upon this Gaussian approximation, it is termed the harmonic approximation.

In a further improvement, the eigenvectors with the smallest eigenvalues are subjected to numerical integrals by a process in which the molecule or complex is distorted stepwise along the eigenvector; at each step, the integrand $\exp(-(U(r)+W(r))/R_gT)$ is computed after each step, and these values are used to compute a numerical estimate of the integral along the eigenvector. If the integral from this numerical scan differs significantly from the analytic integral of the Gaussian, then the numerical result is used in place of the analytic one. Based upon this methodology, a preferred form for the resulting expression for the local configuration integral becomes:

$$Z_i \approx e^{-(U(r_i)+W(r_i))/R_gT}\left(b_2^2 \prod_{l=3}^{N_{atoms}-2} b_l^2 \sin\theta_l\right)\left(\prod_{j=3}^{N_{scan}} S_j\right) \quad \text{Equation 7}$$

$$\left[\prod_{k=1}^{N_{Gaussian}}\left[\left(\left(\frac{2\pi R_g T}{K_k}\right)^{\frac{1}{2}} \text{erf}\left(w_k\left(\frac{2\pi R_g T}{K_k}\right)^{-\frac{1}{2}}\right)\right)\right]\right]$$

Here $b_2$ is the bond-length associated with atom 2, $b_1$ and $\theta_1$ are the bond-length and bond-angle associated with atom 1, the first quantity in parentheses is the Jacobian determinant due to the conversion from Cartesian coordinates to bond-angle-torsion coordinates, and the index l ranges over all but 2 atoms, as previously detailed (Chang et al., J. Phys. Chem. B 107:1048-1055, 2003); T is the absolute temperature; $N_{scan}$ numerical integrals are included and $S_j$ is the numerical integral along eigenvector j; $N_{gaussian}$ analytic integrals are included and the quantity inside square brackets is the analytic integral along eigenvector k; $K_k$ is the eigenvalue associated with eigenvector k, erf is the error function, and $w_k$ is the integration range used along eigenvector k. The integration method associated with Equation 7 is termed harmonic approximation/mode scanning (HA/MS). In the special case where $N_{scan}=0$, then all modes would be integrated harmonically via integrals of Gaussians, and the calculation would use only the harmonic approximation, without any mode scanning. Note that a different system of internal coordinates would require a different Jacobian determinant.

Another advantage of the M2 method derives from its treatment of the solvation energy W(r). As background, it is remarked that the MINTA method uses a generalized Born model (see above) for the electrostatic part of the solvation energy, although this solvation model is known by those skilled in the art to be less accurate than more time-consuming numerical solutions of the Poisson-Boltzmann equation, as discussed above. The M2 method also uses a generalized Born model during its most computationally demanding steps, in order to maximnize efficiency, generating a provisional value of the configuration integral in each energy well $Z_{i,GB}$. However, M2 calculations are then corrected toward the full Poisson-Boltzmann model by carrying out a single Poisson-Boltzmann calculation of the solvation energy $W_{PB}(r_i)$ at each energy minimum $r_i$, as well as a single additional generalized Born calculation of the solvation energy $W_{GB}(r_i)$, and using these data to generate a corrected value of the configuration integral. This strategy takes advantage of the speed of the approximate generalized Born model for most of the calculation, and then makes sparing but effective use of the accurate Poisson-Boltzmann model.

This M2 method has been found to combine excellent accuracy with far greater computational speed than the previous two Local Integration methods. Its accuracy derives from: the empirical fact that energy wells are quite closely approximated by parabolas, and their deviations from parabolic are readily captured by scanning along only the eigenvectors with the lowest eigenvalues; the use of bond-angletorsion coordinates, rather than Cartesian coordinates; and the correction toward a more accurate solvation model. The speed derives from the fact that no random conformational sampling is involved: the method requires nothing more than systematic scanning along eigenvectors with low eigenvalues. Moreover, in many cases, it is found empirically that accurate results are obtained even when this numerical scanning technique is not used; i.e., for the harmonic approximation. Also, the treatment of solvation is both efficient and accurate. For these reasons, the method provides a much better combination of speed and accuracy than prior methods in this class of binding models.

The M2 method, described in the previous paragraphs, has many advantages over its predecessors, and has been found to give good agreement with experimental binding affinities for molecular systems in which both molecules are much smaller than proteins (Chang & Gilson, J. Am. Chem. Soc. 126: 13156-13164, 2004; Chen et al., Biophys. J. 87:3035-3049, 2004; J. Am. Chem. Soc. 128:4675-4684, 2006). However, the method is not applicable to molecules as large as proteins. The chief reason is that a protein has far too many local energy minima i to permit them all to be discovered computationally and integrated by a current computer within an acceptable amount of time. As a consequence, although the M2 method is faster than other Local Integration methods, it still cannot be used for drug-discovery, enzyme engineering, or any other purpose involving a large molecule like a protein. It is an object of the present invention to enable calculation of affinities involving macromolecules.

As discussed above, the energy provided by an empirical force field approximates the energy of more time-consuming and rigorous first-principles quantum mechanics calculations. Empirical force fields are known by those skilled in the art to be particularly inaccurate for certain types of molecules and complexes, notably those which include metal ions, such as the Class B beta-lactamases responsible for many instances of antibiotic resistance in pathogenic microbes. (The Class B beta-lactamases are discussed in, for example, U.S. Pat. No. 5,955,604.) Another object of the present invention is to enable calculations of affinities involving interactions with metal ions.

Some ligands, such as "suicide inhibitors" (for example, U.S. Pat. No. 4,745,109), bind their receptors by forming not only noncovalent interactions but also by forming a covalent bond. In such cases, there is still a need for a computational method of predicting whether one candidate ligand will bind the receptor more tightly than another candidate ligand. However, none of the Local Integration methods previously devised provide a means of predicting the relative affinities of two such covalent ligands. It is yet another object of the present invention to enable accurate calculations of the relative affinity for two candidate ligands that covalently bind a targeted receptor.

In many important cases, the ligand that binds a protein receptor may itself be a large molecule, such as another protein. By way of non-limiting example, the receptor may be an enzyme, the ligand may be another protein that the enzyme cleaves catalytically, and the aim may be to modify the enzyme so that it cleaves a specific protein. Another object of the present invention is to enable the calculation of an affinity when the ligand itself is a macromolecule.

In other important cases, the receptor and/or the ligand is itself a molecular complex consisting of more than one molecule and held together by noncovalent and/or noncovalent forces. Yet an additional object of the present invention is to enable the calculation of affinities when the receptor and/or the ligand is itself a molecular complex.

BRIEF SUMMARY OF THE INVENTION

Certain embodiments of the present invention relate to methods and tools useful for the design and discovery of drug molecules that work by binding targeted macromolecules, such as proteins. Other embodiments of the present invention relate to the design and discovery of targeted binding molecules such as synthetic receptors for applications including drug-delivery, chemical sensing, separation and purification, and self-assembling molecular structures. In specific embodiments, the present invention relates to computational methods of determining how tightly one molecule binds another molecule in solution.

In some embodiments, the present invention provides a novel and improved method for computing the affinity, i.e., the standard free energy of binding, of a receptor and a ligand in solution where one or both of the molecules are macromolecules and may furthermore be multimolecular complexes. The method is based on identifying the low-energy configurations of the receptor-ligand complex, as well as the low-energy configurations of the receptor and ligand in their unbound state. In certain embodiments of the present invention, the calculation of affinities is simplified and accelerated by restraining the conformational variability of part of a macromolecule and treating as fully flexible only key parts, such as the binding site, during the search for low energy configurations. In other embodiments, the present invention provides an efficient method for employing any of a number of high-accuracy energy models without incurring the high computational cost normally associated with such models. In yet other embodiments, the method provides the relative affinities of two ligands that bind the receptor covalently.

In some embodiments, the present invention provides a method for computationally predicting the affinity of a candidate ligand or ligands for a targeted receptor whereby:

1. The receptor, if it is a macromolecule, is partitioned into a part A that will be treated as fully flexible and a part B that will be treated as conformationally restrained. The same partitioning and restraints will be applied to both the free receptor and the receptor in the receptor-ligand complex. The ligand may likewise partitioned. In specific embodiments, the ligand is partitioned when the ligand is a macromolecule.

2. The configuration integral of the free ligand is computed by the following steps.
   a. Computationally identifying $M_L$ local energy minima, using an initial energy function $E(r)$. The set of $M_L$ local energy minima is chosen to be sufficiently extensive that adding additional minima to the calculation produces negligible changes in the configuration integral.
   b. For each energy minimum i, using a numerical method to compute or approximate the local configuration integral $Z_{L,i}$ of the Boltzmann factor, the Mayer factor, or the Andersen factor in the associated energy well, such as by the harmonic approximation in which the energy well is approximated as quadratic in form, or by a more accurate approximation in which the shape of the energy well is ascertained more precisely by evaluating the energy at a selection of points in the vicinity of the energy minimum.
   c. Optionally, for an energy minimum i, computing a more accurate energy $E'(r_i)$ of a conformation representative of the energy well $r_i$, and adjusting the corresponding local configuration integral by the formula $Z_{L,i}^{adj} = e^{-(E'(r_i) - E(r_i))/R_g T} Z_{L,i}$.

c. Summing the optionally adjusted local configuration integrals $Z_{L,i}$ to obtain an estimate of the overall configuration integral of the free ligand $Z_L$.

3. Repeating step 2 for the free receptor R and the receptor-ligand complex RL, in each case identifying and processing a large enough number of energy minima, $M_R$ or $M_{RL}$ respectively, so that processing additional minima produces negligible changes in the respective configuration integrals $Z_R$ and $Z_{RL}$.

4. Computing the standard free energy of binding by the formula $$\Delta G^\circ = -R_g T \ln \left( \frac{C^\circ}{8\pi^2} \frac{\sum_{i=1}^{M_{RL}} Z_{RL,i}}{\sum_{i=1}^{M_R} Z_{R,i} \sum_{i=1}^{M_L} Z_{L,i}} \right)$$  Equation 8 where one or more of the local configuration integrals in the summations have been adjusted according to step 2c.

In one embodiment of the present invention, part B of the receptor or ligand is held rigid in a specified conformation. In another embodiment of the present invention, part B is restrained by an added restoring force that hold the conformation close to a specified conformation. In yet another embodiment of the present invention, the conformationally restrained part of a molecule is restrained to occupy only a small number (e.g. 2) local energy minima. In still a further embodiment of the present invention, the restraint applied to the ligand and/or the receptor during the computational identification of the local energy minima i is removed during the calculation of each local configuration integral $Z_i$.

In some embodiments of the present invention, the harmonic approximation is used to evaluate the local configuration integrals. By way of non-limiting example, the rigid-rotor/harmonic oscillator with or without mass-weighted coordinates, which is well-known to those skilled in the art, is used to evaluate the local configuration integrals. In another embodiment of the present invention, the harmonic approximation/mode scanning method is used for this purpose.

In certain embodiments of the present invention, the energy function E(r) equals the sum of the potential energy from an empirical force field U(r) and the solvation energy from a generalized Born salvation model $W_{GB}(r)$, and E'(r) uses the same empirical force field but uses a more detailed salvation model consisting of a detailed numerical solution of the linearized Poisson-Boltzmann equation plus a nonpolar term related to molecular surface area.

In another embodiment of the present invention, the energy function E(r) uses an empirical force field for the potential energy, and E'(r) uses a quantum mechanical electronic structure calculation to compute the potential energy. In certain specific embodiments, the harmonic approximation of the configuration integral also can be obtained from the quantum mechanical energy function. In yet another embodiment, the methods of thermodynamic integration or free energy perturbation, which are known to those skilled in the art, are used to compute all or part of the solvation part of E'(r).

In some embodiments of the present invention, the ligand, the receptor, or both, comprise multiple molecules held together by noncovalent forces.

In another embodiment of the present invention, the receptor-ligand complex RL includes a covalent bond between the ligand and the receptor. In this case, the relative affinity of ligands 1 and 2, both forming the same type of covalent bond to the same receptor, is computed as $\Delta\Delta G = \Delta G_2^\circ - \Delta G_1^\circ$ where $\Delta G_1^\circ$ and $\Delta G_2^\circ$ are computed as above.

In certain embodiments of the present invention, the conformation of a molecule or complex is specified by bond-angle-torsion coordinates. In some of these embodiments, the position and orientation of the ligand relative to the receptor in their complex are defined by creation of a pseudo-bond linking one atom of the ligand to one atom of the receptor. In another embodiment, Cartesian coordinates are used, and the rigid rotor/harmonic oscillator approximation is used to computing the local configuration integrals.

Thus, certain embodiments of the present invention provide a method of predicting the affinity of a molecule for a protein or other type of macromolecule, that combines accuracy and speed. It will thus be useful in the pharmaceutical, chemical and other industries to speed the discovery of targeted molecules for use as medicines, catalysts, separation agents, etc.

DETAILED DESCRIPTION OF THE INVENTION

Definitions

Figure 1:
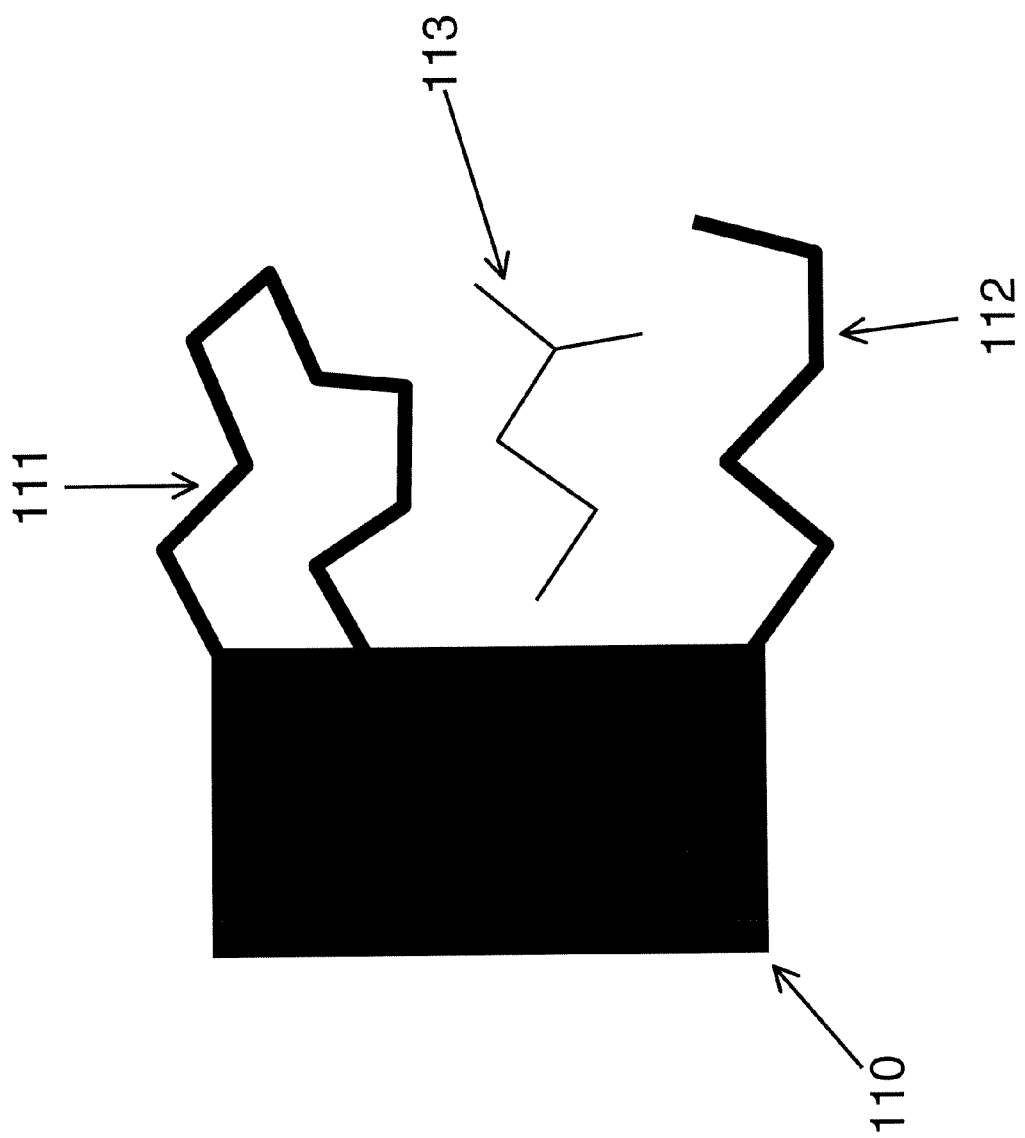
FIG. 1. According to an embodiment of the present invention, a diagram of a macromolecular receptor with a bound ligand, where the receptor is partitioned into a restrained part and a mobile part. The mobile part here furthermore comprises a mobile loop both of whose ends are anchored in the restrained part, and a mobile chain one of whose ends is anchored in the restrained part.

The following terms, and the theoretical aspects of the present invention which they convey, are generally accepted by those skilled in the art. They are summarized here for the sake of clarity.

Andersen factor: a factor similar to the Boltzmann and Mayer factors that is computed by separating the energy into a strongly repulsive part $E_R$, typically associated with steric interactions, and a residual attractive part $E_A$, such that the total energy $E = E_R + E_A$, and then formulating the Andersen factor as $e^{-E_A/(R_G T)} - e^{-E_R/(R_G T)}$, where $R_G$ is the gas constant and T is absolute temperature.

Boltzmann factor: the exponential of the energy E divided by either Boltzmann's constant or, as used here, the gas constant $R_g$, times the absolute temperature T: $e^{-E(r)/(R_g T)}$, where E may also be separated into a potential energy part U and a solvation energy part W: $e^{-(U(r)+W(r))/(R_g T)}$.

Bond-angle-torsion coordinates: a set of internal coordinates in which the location of an atom i is specified in terms of its relation to 3 other atoms j,k,l, where covalent bonds exist between atoms i and j, j and k, and k and l. The location of atom i is defined by the distance $b_{ij}$, the angle $\theta_{ijk}$ and the dihedral (torsion) angle $\phi_{ijkl}$.

Candidate ligand: a small molecule whose affinity for a targeted receptor is to be calculated.

Cartesian coordinates: a coordinate system in which the position of an atom is specified by customary x,y,z coordinates.

Complex: A plurality of molecules held together by noncovalent and potentially covalent forces and considered as a unit. By way of non-limiting example: 1) a receptor with a bound ligand is a complex; 2) a receptor that consists of two proteins held together by noncovalent forces is a complex; 3) a receptor that consists of a protein and a small molecule held together by at least noncovalent forces is a complex. Note that the complex receptors identified in (2) and (3) can both, by definition, further bind a ligand to form a still larger complex. In some embodiments, the complex may comprise a plurality of molecules held together by a combination of covalent and noncovalent forces.

Configuration: three dimensional structure of a molecular system defined by the relative locations of all the atoms in space; e.g., by a set of internal coordinates.

Configuration integral: typically the integral of the Boltzmann factor over molecular coordinates. Here, the term is intended to encompass as well the integral of the Boltzmann factor over both molecular coordinates and momenta in the case of the rigid rotor/harmonic oscillator approximation, as well as the integral of related integrands such as the Mayer or Andersen factors.

Conformation: same as configuration.

Energy: the energy of a molecule or complex as a function of its configuration, typically including contributions from bond-stretching, angle-bending, rotation of torsion angles, van der Waals interactions among atoms and electrical interactions among atoms, as well as contributions from the solvent (often water) in which the molecule or complex is immersed. The energy can be defined with respect to a situation in which the ligand and receptor do not interact with each other, or with respect to other real or hypothetical reference states.

Energy model: a mathematical function E(r) for computing the energy of a molecule or complex in a given conformation. In some embodiments, the given conformation is defined by the internal coordinates r, typically including both a potential energy part U(r) and a solvation energy part W(r), such that $E(r)=U(r)+W(r)$.

Energy well: the configurations immediately surrounding a local energy minimum.

External coordinates: a set of 6 coordinates that specify the position and orientation of a molecular system in space.

Free ligand: a ligand that is not bound to a receptor

Free receptor: a receptor that is not bound to a ligand

Harmonic approximation: the approximation that the energy in the vicinity of a local energy well varies quadratically with the distance of a conformation from a lowest point of the energy well. Thus, the harmonic approximation treats the energy well as having a parabolic shape. The coefficients of this multidimensional parabola form the matrix of second derivatives of the energy with respect to the internal coordinates of the molecule. Implicit solvent model: a computer model that provides the solvent (e.g. water) part of the energy of a molecule as a function of the configuration of the molecule. An implicit solvent model can also include a number of explicitly treated solvent models; such an implicit solvent model is sometimes termed a hybrid solvent model.

Internal coordinates: for a molecular system with $N_{atom}$ atoms, a set of $3N_{atom}-6$ coordinates that specify its conformation.

Ligand: a molecule that binds a receptor, often by noncovalent forces, but sometimes by a combination of covalent bonding and noncovalent forces.

Local energy minimum: a configuration of a molecular system for which the energy is a local minimum; i.e., for which the first derivative of the energy with respect to the motion of any atom treated as mobile (see below) is zero and the eigenvalues of the matrix of second derivatives of the energy with respect to the motion of all such atoms are all greater than zero.

Mayer factor: the Boltzmann factor (defined above) minus 1; e.g., $e^{-E(r)/(R_gT)}-1$.

Macromolecule: a large molecule often of biological origin, usually a protein but also potentially another type, such as DNA or RNA, and often possessing a binding site so that it can act as a receptor.

Molecular system: a ligand, a receptor or a complex.

Molecule: a set of atoms held together by covalent bonds

Pseudo-bond: a notional bond between two atoms that are not covalently bonded to each other, which is defined for the purpose of extending a bond-angle-torsion system of coordinates from one molecule in a complex to a second molecule in the complex; e.g., from a receptor to a bound ligand.

Receptor: a molecule that binds a ligand. It is also intended herein that a receptor can be construed as a multimolecular complex.

Small molecule: a molecule whose molecular weight is lower than that of a typical protein. In some embodiments, a small molecule has a molecular weight of less than 1000 Daltons. In specific embodiments, a small molecule has a molecular weight of less than 500 Daltons.

Standard binding free energy: The change in free energy $\Delta G^\circ$ when ligand at standard concentration and receptor at standard concentration but with activity coefficients hypothetically set to unity bind to form complex also at standard concentration and with an activity coefficient of unity. This standard binding free energy has units of energy, such as kcal/mol, and is a measure of the affinity of the ligand and the receptor for each other: the more negative the standard binding free energy the greater the affinity. In one embodiment, the present invention is utilized to calculate this measure of affinity or to calculate the difference between the standard binding free energy, $\Delta\Delta G^\circ$ of two different ligands for the same receptor. In some embodiments of the present invention, the relative binding affinity or relative binding free energy may describe this difference.

Standard concentration: The concentration of ligand, receptor and complex for which standard chemical potential and standard binding free energy are defined. Standards-setting organizations, such as the International Union of Pure and Applied Chemistry, have chosen 1 mole/liter (1 M) as the standard concentration of molecules in solution.

Thermodynamic integration and free energy perturbation: Rigorous and relatively time-consuming computational methods for evaluating the difference in free energy between two states of a system via molecular simulations. These methods can be used to compute the solvation free energy W(r) of a molecular system in a given configuration r, or to compute part of the salvation energy, such as the electrostatic part.

Introduction of Macromolecular Restraints

An innovation of certain embodiments of the present invention is to make the M2 method of computing binding affinities, and related methods, computationally tractable when the receptor and optionally the ligand are macromolecules and hence too large to permit enumeration of all of its low-energy conformations. In some embodiments of the present invention, this problem is overcome by restraining part of the macromolecule in a conformation that is known to be physically relevant (See, e.g., FIG. 1). To the extent that the conformation of part B does not readjust when a ligand binds, it can be held fixed or restrained in a narrow range of conformations during the binding calculations without changing the computed binding affinity.

FIG. 1 diagrams one possible partitioning of a macromolecular receptor (110, 111, 112) with a bound ligand (113), where the receptor is partitioned into a restrained part (110) and a mobile part comprising in this case a mobile loop (111), both of whose ends are covalently bound to the restrained part (110) and a mobile chain (112), one of whose ends is covalently bound to the restrained part (110).

In some cases, a substantial part of a receptor changes conformation when a ligand binds. For such receptors, it can be difficult to identify a suitable part B that can be restrained without introducing error into the standard free energy of binding. However, it is frequently true for such receptors that the conformation of much of the protein, again termed part B, remains essentially unchanged when one bound ligand is substituted for another. It can readily be shown theoretically that, in such cases, the difference between the binding free energy of the two ligands, $\Delta\Delta G^\circ$, can still be accurately computed as the difference between the binding energies $\Delta G^\circ$ computed with part B held fixed or restrained. Therefore, affinities computed as $\Delta G^\circ$ can still be used to compare the affinities of different ligands for the same receptor, and therefore can still be used to guide drug-discovery or other projects in molecular design.

Precisely the same considerations apply when the ligand is a macromolecule, and restraints can be applied to a part B the ligand on the same basis.

Based upon these considerations, in certain embodiments of the present invention, Part B of the receptor or ligand is restrained by rigidly fixing it in a conformation that is experimentally observed or that is obtained from a separate computer model. In other embodiments of the present invention, part B is restrained by supplementing the energy as a function of conformation with an additional restraint term $E^{rstrnt}(r)$, whose energy rises as the conformation deviates from the desired conformation of part B. These embodiments of the present invention allow for a small amount of flexibility, which can increase the accuracy of the calculations relative to rigidly fixing part B, at low computational cost. In particular, if the restraint term is large enough, part B will access only one low-energy conformation. In a specific embodiment of the present invention, the restraint energy is harmonic; i.e., it rises quadratically with this deviation, where the deviation is defined in bond-angle-torsion coordinates (see, e.g., FIG. 3) or in Cartesian coordinates. In certain embodiments of the present invention, the force constants of the restraints are derived from the matrix of second derivatives of the energy of the receptor, while in another aspect the force constants are obtained from elastic or Gaussian Network models of proteins familiar to those skilled in the art. In another embodiment of the present invention, part B is allowed to access a small number of distinct local energy minima. For example, an allosteric enzyme can be allowed to access its two chief allosteric conformations as determined by crystallographic studies.

Restraining part of a macromolecule according to certain embodiments of the present invention makes calculation of the configuration integral as a sum of local configuration integrals (e.g. Equation 5) tractable by reducing the number of local energy minima that need to be identified and evaluated by local integration. However, computing a local configuration integral when the entire macromolecule is treated as mobile (unrestrained) is computationally tractable in many cases and has the potential to increase accuracy. Therefore, in another embodiment of the present invention, the configuration integrals are computed with some or all restraints removed. In such embodiments, all or part of the system may be subjected to computational energy-minimization before evaluation of the configuration integral so that configuration integration is centered on a true local energy minimum.

Incorporation of Accurate Energy Models

An innovation of certain embodiments of the present invention is a provision for incorporating any of a number of high accuracy energy models into a binding energy calculation at low computational cost. In some embodiments of the present invention, this is accomplished by carrying out an initial search for energy minima and computing initial local configuration integrals with a fast energy model, such as an empirical force field combined with the generalized Born model for salvation, and then correcting each local configuration integral toward a more accurate energy model by means of an energy calculation for only a single representative conformation in the energy well. In certain embodiments of the present invention, the energy minimum conformation $r_i$ of the energy well, based upon the initial energy model, is used as the representative conformation. In some embodiments, the correction is then made as follows. If the initial local configuration integral for energy well i is $Z_i$, the initial energy of the energy minimum is $E(r_i)$, and the more accurate energy is $E'(r_i)$, then the adjusted configuration integral is $Z_i^{adj} = e^{-(E'(r_i) - E(r_i))/R_g T} Z_i$. This expression effectively shifts the energy well so that its minimum lies at $E'(r_i)$ instead of $E(r_i)$, without changing its conformation or the shape of the energy surface. This adjustment is illustrated in FIG. 2.

Figure 2:
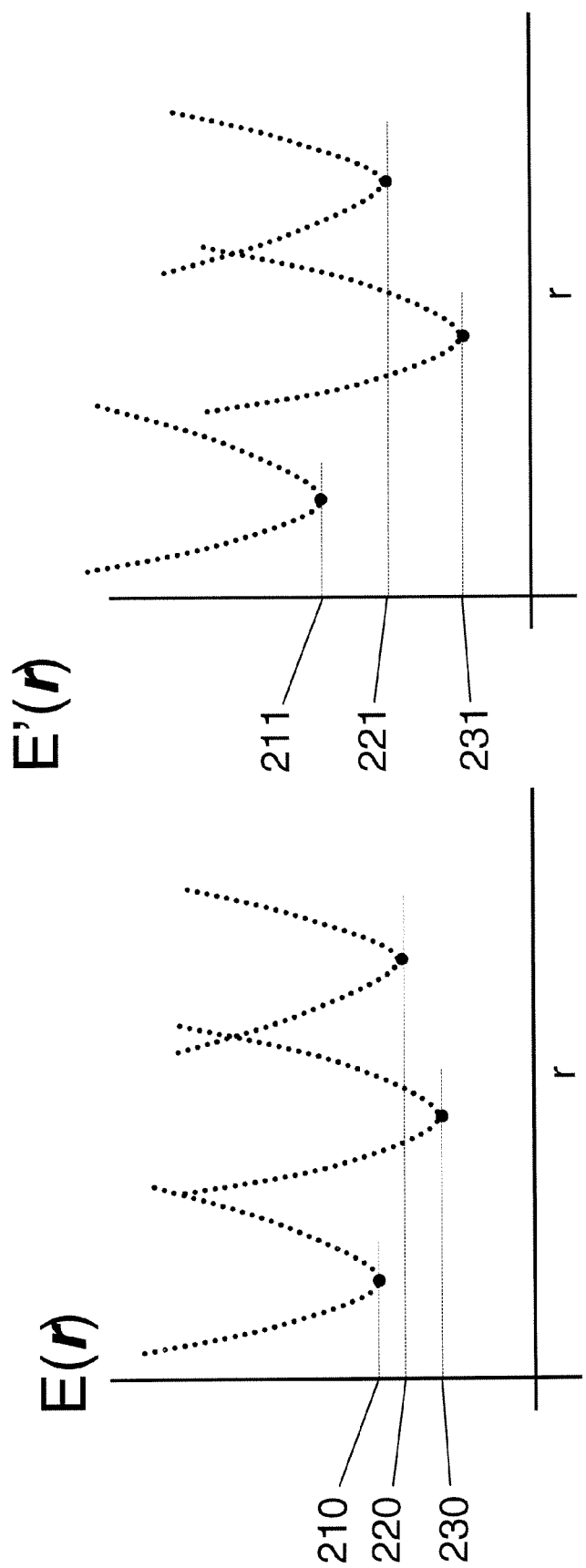
FIG. 2. According to an embodiment of the present invention, a diagram of an adjustment of energy wells from E(r) to E'(r) by adding $E'(r_i) - E(r_i)$ to the harmonic approximation to each energy well, thus shifting each well up or down in energy without moving or changing its shape.

FIG. 2 illustrates the shifting of the initial energies of the harmonic approximations to three local energy wells by computing the energies $E(r_1)$ (210), $E(r_2)$ (220) and $E(r_3)$ (230), and then shifting each parabola, without any change in its shape, so that the local minima now lie at $E'(r_1)$ (211), $E'(r_2)$ (221) and $E'(r_3)$ (231).

In certain embodiments of the present invention, a more accurate model for the potential energy is substituted for an initial energy computed with an empirical force field. In a specific embodiment, the more accurate potential energy model uses quantum mechanical electronic structure calculations, such as Hartree-Fock or Density Functional Theory calculations. In another specific embodiment of the present invention, the solvation energy or part thereof is computed by the method of thermodynamic integration or the method of free energy perturbation using an explicit solvent model.

Complex Receptor or Ligand

In another embodiment of the present invention, the receptor can itself be a complex of multiple molecules held together by noncovalent and/or covalent forces. For example, the receptor might be the enzyme dihydrofolate reductase, which typically exists as a complex with the cofactor NADPH; this complex then binds a small molecule ligand, such as the drug methotrexate. In such cases, part B of the receptor may encompass none, part, or all of a given molecule within the receptor, depending upon what is known about the conformational changes of each molecule when a ligand binds the receptor. The same approach can be used for a ligand that is itself a complex of multiple molecules held together by noncovalent forces.

Covalently Bonding Ligands

An empirical force field typically provides inaccurate results for the energy change associated with formation of a covalent bond. Therefore, in some embodiments, the value of $\Delta G^\circ$ computed by the present invention with an empirical force field is likely to be inaccurate for a ligand that forms a covalent bond with its receptor. However, when the same type of covalent bond is formed by two such ligands, the error due to the empirical force field is essentially the same in both cases and will cancel when a difference is taken. Therefore, in another embodiment of the present invention, the relative affinity $\Delta\Delta G^\circ$ of two such ligands, ligands 1 and 2, for the same receptor is computed accurately as $\Delta\Delta G = \Delta G_2^\circ - \Delta G_1^\circ$ where $\Delta G_1^\circ$ and $\Delta G_2^\circ$ are computed according to the procedures already described. Such a relative binding affinity can be used to determine which of the two ligands is preferred in a molecular design project and thus still serves the overall purpose of the present invention.

Additional Aspects of the Invention

In a specific embodiment of the present invention, the local configuration integrals are computed with the harmonic approximation, where the integration domains are infinite. In another embodiment, the local configuration integrals are computed with the harmonic approximation (see, e.g., FIG. 4), where the integration domains are established by diagonalizing the second derivative matrix of the energy with respect to the conformation, determining the standard deviation of the Gaussian probability distribution along each eigenvector based upon the corresponding eigenvalue and the temperature, and limiting the integration domain along each eigenvector to a specified number of standard deviations of the Gaussian. In yet another embodiment of the present invention, the local configuration integrals are computed using the rigid rotor/harmonic oscillator approximation with a Cartesian basis set. In this case, the local configuration integrals are computed according to a different formula that correctly accounts for the special coordinate system implicit in this approximation, such as:

$$Z_i \approx \left[\left(\frac{2\pi M R_g T}{h^2}\right)^{\frac{3}{2}}\right]\left[\left(\frac{2\pi M R_g T}{h^2}\right)^{\frac{3}{2}} (I_{a,i} I_{b,i} I_{c,i})^{\frac{1}{2}}\right] \quad \text{Equation 9}$$

$$\left[\left(\frac{2\pi M R_g T}{h^2}\right)^{\frac{3N_{atoms}-6}{2}} Z_i^{vib}\right]$$

where M is the total mass of the molecule, h is Planck's constant, $I_{a,i}$, $I_{b,i}$ and $I_{c,i}$ are the principle moments of rotational inertia of the molecule in conformation i, and $Z_i^{vib}$ is the configuration integral over the mass-weighted internal (vibrational) coordinates associated with the rigid rotor/harmonic oscillator approximation (Potter & Gilson, J. Phys. Chem. A 106:563-566, 2002). Such an approach is particularly suitable when a quantum mechanical energy adjustment is employed because the quantum mechanical calculations readily yield the quantities required to evaluate the local configuration integral with the rigid rotator/harmonic oscillator approximation.

Figure 3:
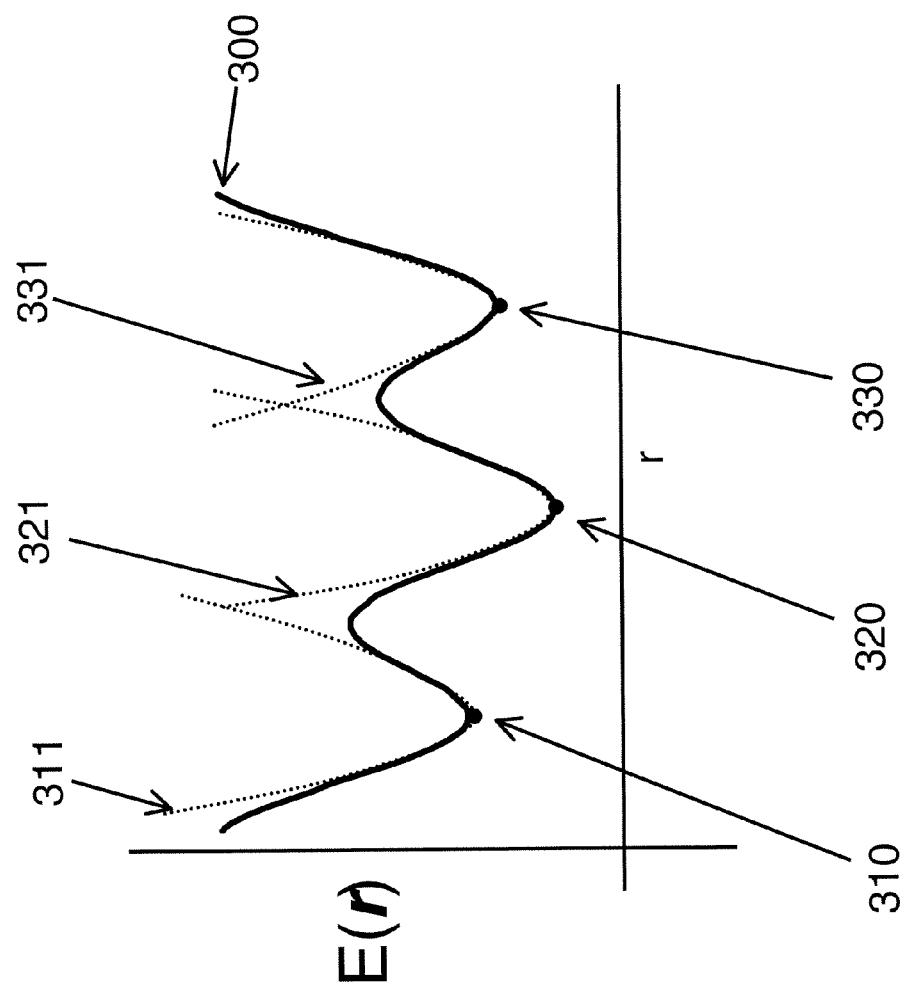
FIG. 3. According to an embodiment of the present invention, a diagram of harmonic approximations (dotted lines) to three energy wells surrounding local energy minima (filled circles) 1 2 and 3 in the E(r) energy surface.

FIG. 3 illustrates an embodiment of the harmonic approximation to for an energy surface E(r) (300) having three local energy minima (310, 320, 330). Three parabolas (311, 321, 331) correspond to the harmonic approximations to the energy in the vicinity of the three respective local energy minima.

Certain embodiments of the present invention include a step of identifying local energy minima. Many existing computational methods are suitable for this step. In one embodiment of the invention, the Tork conformational search method is used (Chang & Gilson J. Comput. Chem. 24:1987-1998, 2003). In other embodiments of the present invention, simulated annealing, quenched molecular dynamics, or other specific methods are used for this step.

In a specific embodiment, the present invention provides a method for predicting the affinity of a candidate ligand for a macromolecular receptor comprising:

a) partitioning the receptor into a part A that will be treated as fully flexible and a part B whose flexibility will be restrained, for both the free receptor and its complex with the ligand;

b) partitioning the ligand into a part A that will be treated as fully flexible and a part B whose flexibility will be restrained, where part A may comprise the entire ligand, and where the same restraints will be applied to both the free ligand and the ligand in its complex with the receptor;

c) using a computational method with initial energy model E(r) to identify $M_R$ local energy minima of the free receptor restrained according to (a);

d) computing the local configuration integral $Z_{R,i}$ in the vicinity of each energy minimum of the free receptor found in (c), with energy model E(r), optionally with some or all of the restraints removed;

e) using a computational method with initial energy model E(r) to identify $M_L$ local energy minima of the free candidate ligand restrained according to (b);

f) computing the local configuration integral $Z_{L,i}$ in the vicinity of each energy minimum of the free ligand as found in (d), with energy model E(r), optionally with some or all of the restraints removed;

g) using a computational method with initial energy model E(r) to identify $M_{RL}$ local energy minima of the complex of the ligand and the receptor, restrained according to (a) and (b);

h) computing the local configuration integral $Z_{RL,i}$ in the vicinity of each energy minimum of the receptor-ligand complex as found in (g), with energy model E(r), optionally with some or all of the restraints removed;

i) optionally adjusting the value of a local configuration integral $Z_i$ computed in (d), (f), and/or (h) by recalculating the energy E(r) for a single conformation $r_i$ associated with local energy minimum i and also with a second energy model E'(r) and calculating the adjusted configuration integral as $Z_i^{adj} = e^{-(E'(r_i)-E(r_i))/R_g T} Z_i$;

j) computing the standard free energy of binding as $$\Delta G^\circ = -R_g T \ln \left( \frac{C^\circ}{8\pi^2} \frac{\sum_{i=1}^{M_{RL}} Z_{RL,i}}{\sum_{i=1}^{M_R} Z_{R,i} \sum_{i=1}^{M_L} Z_{L,i}} \right)$$

where one or more local configuration integrals $Z_{RL,i}$, $Z_{R,i}$ or $Z_{L,i}$ may have been adjusted according to (i).

In certain embodiments of the present invention, the affinity of a candidate ligand for a receptor is output following the computation of the energy of binding of the ligand to the receptor. In some embodiments of the present invention, the affinity output is an absolute affinity value. In other embodiments of the present invention, the affinity output is a relative affinity value of one ligand for the receptor relative to the affinity of another ligand for the same receptor. In specific embodiments of the present invention, the affinity is output as the standard free energy of binding. In another specific embodiment of the invention, the affinity is output as a normalization of the standard free energy of binding.

In some embodiments, the present invention includes adjusting the value of the local configuration integral computed in the vicinity of each energy minimum identified for one or more of a candidate ligand, a receptor and a receptor-ligand complex. In specific embodiments of the present invention, the process of adjusting the value of a local configuration integral can be carried out computationally by recalculating the energy with a first energy model for a single confirmation $r_i$ associated with local energy minimum i and also with a second energy model, and calculating the adjusted configuration integral as $Z_i^{adj} = e^{-(E'(r_i) - E(r_i))/R_g T} Z_i$. The terms $Z_i$ and $Z_i^{adj}$ are, respectively, the unadjusted configuration integral based upon the first energy model and the configuration integral adjusted toward the second energy model. Similarly, $E(r_i)$ and $E'(r_i)$ are, respectively, the energy of the conformation $r_i$ computed with the first and second energy models. $R_g$ is the gas constant and T is absolute temperature.

Note that the Boltzmann factor can also be written with Boltzmann's constant $k_b$ substituted for $R_g$ and with other quantities also consistently rewritten on a per-molecule rather than a per-mole basis. Note, too, that minor variants of the Boltzmann factor have been used to formulate theories of binding. The variants include the Mayer factor and what can be termed the Andersen factor, as published elsewhere (Mihailescu & Gilson, Biophys. J. 87:23-36). In the present invention, such variants are considered to be equivalent to the Boltzmann factor and they can be used instead of the Boltzmann factor within the scope of the present invention.

In certain embodiments of the present invention, atomic coordinates of the ligand, the receptor, and their complex, are defined in terms of Cartesian coordinates, while in other embodiments, atomic coordinates are defined in terms of bond-lengths, bond-angles, and bond-torsions. In certain embodiments, the position and orientation of the ligand with respect to the receptor, can be defined in terms of Cartesian coordinates and rotation angles, while in other embodiments, the position and orientation of the ligand with respect to the receptor are specified via formation of a pseudobond between an atom of the receptor and an atom of the ligand. In certain embodiments, this pseudobond is used in the context of bond-angle-torsion coordinates, as illustrated in FIG. 4.

Figure 4:
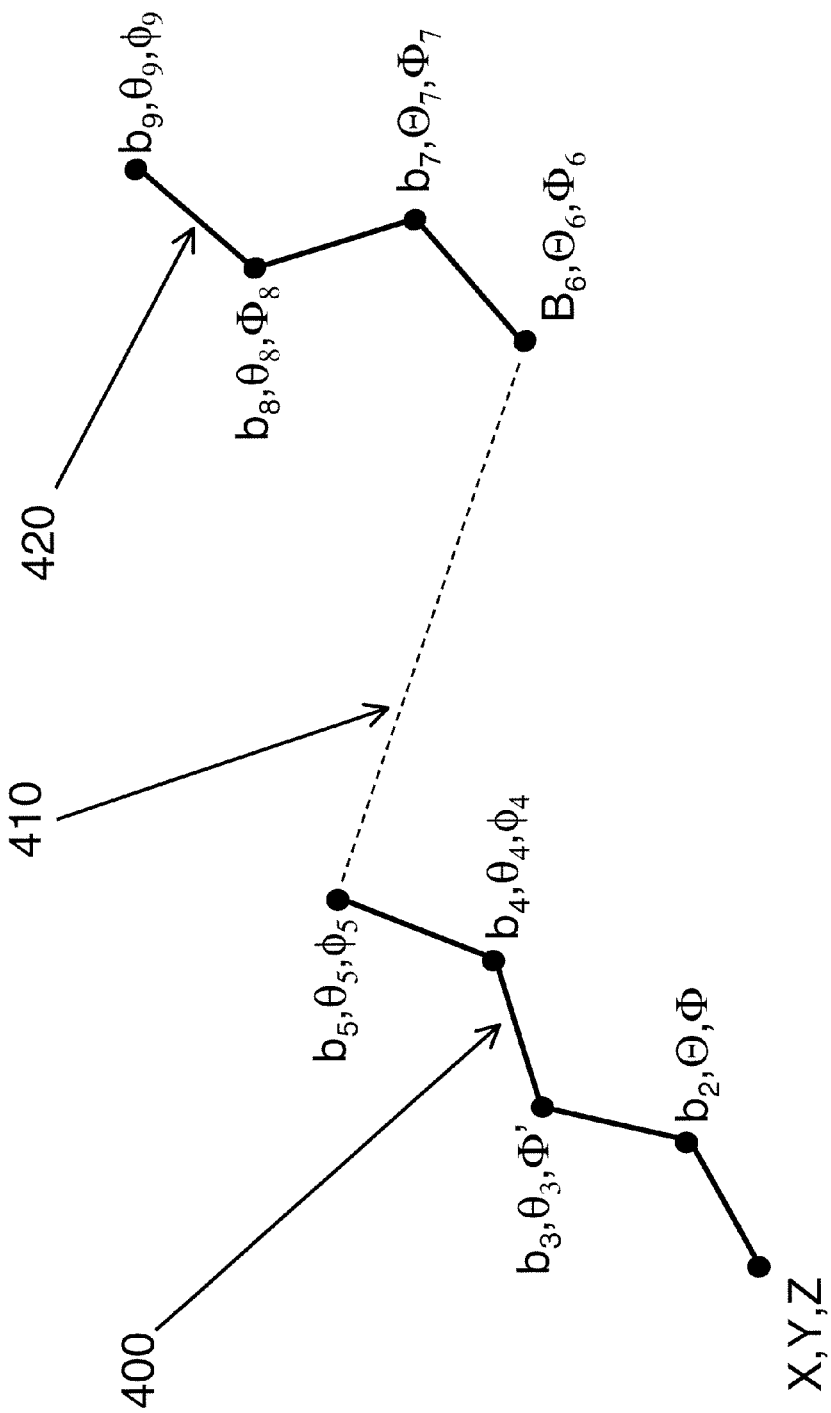
FIG. 4. According to an embodiment of the present invention, a diagram of bond-angle-torsion coordinates for a receptor ligand complex, including a pseudobond used to define the position and orientation of the ligand with respect to the receptor.

FIG. 4 illustrates one embodiment of the use of a pseudobond to fully define the spatial coordinates of a simplified receptor-ligand complex. The position of the receptor (400) is specified by the Cartesian coordinates (X,Y,Z) of the leftmost atom. Its orientation in space is specified by the direction of the first bond-vector, shown as $\Theta,\Phi$, along with the angle $\Phi'$ which defines a body-rotation of the molecule. The coordinates of subsequent atoms in the receptor are defined in terms of a bond-length b, an angle $\theta$, and a dihedral angle $\phi$, defined with respect to the previous three atoms of the molecule, going from left to right. The pseudobond (410), shown as a dashed line, allows the coordinates of the atoms of the ligand (420) as well to be defined as bond-lengths, bond-angles, and dihedral angles defined with respect to the previous three atoms of the ligand or receptor, where the pseudobond is treated as a real bond purely for the purpose of building this coordinate system. In particular, the pseudobond makes no contribution to the energy of the complex.

The various calculations, comparisons, and judgments required during operation of embodiments of the present invention may be accomplished by conventional computer hardware or software. These calculations are preferably performed automatically during the normal course of operation of embodiments of the present invention. By way of non-limiting example, the computations and comparisons associated with equations 1-9 may be performed by appropriately programmed or configured standard computer hardware or software.

Inputs and Outputs of Certain Embodiments of the Invention

This section summarizes certain inputs and outputs that may be used in certain embodiments of the present invention. First, an input used in some embodiments of the present invention is the chemical structure of the receptor and the ligand. If the ligand is a small molecule, then no initial three-dimensional conformation of the ligand is required as an input, because the method will automatically generate the required low-energy conformations. However, the present method does not provide a method of establishing a relevant conformation of a macromolecular receptor at atomic spatial resolution. Therefore, such an initial conformation must be provided by the user. In one mode of operation, such needed structures are obtained from a structural database like the Protein Data Bank (PDB; www.pdb.org), or by new Xray crystallographic studies or by high-resolution nuclear magnetic resonance studies. For example, if the targeted protein is the enzyme acetylcholinesterase, a suitable initial conformation could be the PDB entry 2J4F (www.pdb.org/pdb/explore.do?structureId=2J4F).

One aspect of certain embodiments of the present invention is that the conformation of part of a macromolecular receptor is restrained during the search for local energy minima. Therefore, another input used in certain embodiments of the present invention is a specification of what part of the receptor is to be conformationally restrained, and in what way it is to be restrained. In some embodiments, this information is obtained by analysis of existing atomic resolution structures, such as crystal structures, of the receptor by itself and in complex with various ligands. In specific embodiments of this approach, a part of the receptor whose conformation changes little on binding a ligand might be conformationally constrained during the calculations. Alternatively, test calculations with various restraints, aimed at reproducing measured binding affinities of a given receptor with a set of ligands of known affinity, can be used to establish suitable restraints for a given receptor. In certain embodiments of the present invention, these restraints are then used to predict the affinities of new candidate ligands.

In another embodiment of the present invention, the potential energy U(r) of the molecules as a function of conformation r is computed with an empirical force field. Various such force fields are known to those skilled in the art, such as the protein and nucleic acid force fields associated with the simulation programs CHARMM (Brooks et al., J. Comput. Chem. 4:187-217, 1983) and AMBER (Weiner at al., J. Am. Chem. Soc. 106:765-784, 1984), as well as force fields that are applicable to a broader variety of molecules, such as Dreiding (Mayo et al., J. Phys. Chem. 94:8897-8809, 1990). Each force field is associated with a set of parameters, such as atomic charges, and these parameters are additional inputs to the model. Other embodiments of the present invention use quantum mechanical methods to compute the potential energy, and these are associated with their own parameters. In certain embodiments of the present invention, implicit solvent models are used to compute the salvation energy W(r) as a function of molecular conformation r, and an implicit solvent model also is associated with certain parameters.

Additional inputs for use in some embodiments of the present invention specify details of how the calculation is to be performed. For example, in certain embodiments of the present invention, the search for local energy minima includes a stopping criterion. When this criterion is met, the search for new local energy minima ceases. In specific embodiments of the present invention, the search ceases when it is found that accounting for a new set of energy minima produces a negligible change in the configuration integral. The definition of what is a negligible change is an additional parameter of the method. By way of non-limiting example, a widely accepted aim among those skilled in the art is to compute binding free energies accurate to within 1 kcal/mol of the experimentally measured binding free energy. Therefore, in certain embodiments of the present invention, it is appropriate to choose a stopping criterion such that accounting for more energy minima is unlikely to change the computed binding free energy by more than 1 kcal/mol. In one embodiment of the invention, this is accomplished by continuing to search and incorporate new energy minima until the most recently added 5 energy minima lead to a change in the computed free energy that is less than 0.1 kcal/mol.

In certain embodiments of the present invention, an output is a calculated value of the standard free energy of binding $\Delta G^o$ of the receptor and ligand. In other embodiments, an output is the relative free energy of binding $\Delta\Delta G^o$ of two ligands for the same receptor, or two receptors for the same ligand. In specific embodiments, the present invention also lists each local energy minimum i that has been found, along with its local configuration integral $Z_i$ which is a measure of its stability, such that the ratio of the probability $p_i$ of a molecular system existing in conformation i to the probability $p_j$ of existing in conformation j is given by $$\frac{p_i}{p_j} = \frac{Z_i}{Z_j}.$$

Applications of the Invention

In certain embodiments, the present invention is used to identify molecules that will bind a targeted receptor with high affinity. Such molecules may be used in biomedical applications as modulators (agonists, antagonists, enhancers, inverse-agonists) of enzymes, receptors, lymphokines, cytokines, growth factors, regulatory molecules, transcription factors, and target nucleic acid sequences such as DNA and RNA molecules, e.g. nucleic acid sequences specific to pathogens or genes the activity of which is desirably modulated. These ligands may be useful as therapeutics alone or in combination with other therapeutics. These ligands may also be used to analyze biological systems in a research setting rather than a clinical setting by ascertaining the consequences of such modulation. These ligands may be small molecules such as peptides or drug-like compounds, or they may be macromolecules or multimolecular complexes. They may bind the receptor via only noncovalent forces, or by a combination of covalent bonding and noncovalent forces.

In other embodiments, the present invention is used to identify synthetic or artificial receptors. In specific embodiments of this application, it is desirable to discover a receptor that will bind a targeted ligand. Many candidate receptors could be made and tested; these embodiments of the present invention allow these candidate receptors to be tested computationally and thus obviate the need to test many candidate receptors experimentally. Such embodiments, therefore, save both time and money. Synthetic receptors are useful as reagents for affinity purification and for ligand detection. Alternatively, such synthetic receptors are combined or mixed with a ligand e.g., a drug, in order to produce a ligand/receptor complex that may be more stable or soluble in a desired environment, e.g., in vivo or in vitro environment than the ligand e.g., a drug alone. Also, such ligand/receptor complexes are useful in studying ligand/receptor interactions and in screens for identifying molecules that modulate ligand/receptor interactions.

In yet other embodiments, the present invention is used in enzyme engineering. For example, if a chemical company knows of an enzyme that catalyzes a useful chemical reaction, but the enzyme binds and acts on a substrate different from the one of interest, it is then desirable to change the enzyme so that it binds the intended substrate and then catalyzes the intended reaction. Such embodiments are useful in this application because they allow proposed changes to the enzyme to be tested computationally rather than experimentally, and hence save time and money.

Certain embodiments of the present invention are uniquely suited to computing the affinity of a ligand for a protein containing a metal ion, such as a zinc ion, such that the ligand interacts directly with the metal ion. Such binding reactions are notoriously difficult to analyze by existing techniques. The energy adjustment aspect of the subject invention provides a means of accounting for the quantum mechanical intricacies of ligand-metal interactions within the framework of a rigorous statistical mechanical treatment of binding.

In still other embodiments, the present invention includes the capability of comparing the affinities of ligands that bind a receptor covalently. This capability becomes important when, for example, the covalent bond is labile so that the free and bound ligands are in equilibrium. For example, a disulfide bond may be able to break and reform and hence to equilibrate on a relevant time-scale.

The equations contained in this disclosure are illustrative and representative and are not meant to be limiting. Alternate equations may be used to represent the same phenomena described by any given equation disclosed herein. In particular, the equations disclosed herein may be modified by adding error-correction terms, higher-order terms, or otherwise accounting for inaccuracies, using different names for constants or variables, or using different expressions. Other modifications, substitutions, replacements, or alterations of the equations may be performed It is noted that the foregoing examples have been provided merely for the purpose of explanation and are in no way to be construed as limiting of the present invention. While the present invention has been described with reference to certain embodiments, it is understood that the words which have been used herein are words of description and illustration, rather than words of limitation. Changes may be made, within the purview of associated claims, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses.

We claim:

1. A method for predicting the affinity of a ligand for a receptor comprising the steps of:
    (a) selecting a ligand;
    (b) selecting a receptor;
    (c) selecting a first and a second portion of said receptor, wherein said portions are putatively involved in ligand binding;
    (d) identifying at least one first local energy minimum for conformations of the ligand by using a computation method with a first energy model;
    (e) identifying at least one second local energy minimum for conformations of the receptor by using a computation method with a second energy model,
        wherein the first portion of said receptor is treated as restrained and the second portion of said receptor is treated as unrestrained;
    (f) identifying at least one third local energy minimum for conformations of a complex of said receptor and said ligand, wherein said receptor is complexed to said ligand, by using a computation method with a third energy model,
        wherein the first portion of said receptor is treated as restrained and the second portion of said receptor is treated as unrestrained;
    (g) computing an energy of binding, using computer hardware or software,
        between the ligand and the receptor, based on the first, second and third energy minima; and
    (h) outputting an affinity of the ligand for the receptor.

2. The method of claim 1, further comprising one or more of the following steps:
    a. computing a first set of local configuration integrals, each local configuration integral computed in the vicinity of a local energy minimum identified in said step of identifying the at least one first local energy minimum;
    b. computing a second set of local configuration integrals, each local configuration integral computed in the vicinity of a local energy minimum identified in said step of identifying the at least one second local energy minimum; and
    c. computing a third set of local configuration integrals, each local configuration integral computed in the vicinity of a local energy minimum identified in said step of identifying the at least one third local energy minimum.

3. The method of claim 2, wherein the step of computing an energy of binding between the ligand and the receptor comprises computing:

$$\Delta G^\circ = -R_g T \ln \left( \frac{C^\circ}{8\pi^2} \frac{\sum_{i=1}^{M_{RL}} Z_{RL,i}}{\sum_{i=1}^{M_R} Z_{R,i} \sum_{i=1}^{M_L} Z_{L,i}} \right)$$

wherein $\Delta G^\circ$ is the standard free energy of binding; $R_g$ is the gas constant; T is the absolute temperature; $C^\circ$ is the standard concentration; $M_{RL}$ is the number of local energy minima of the complex used in the step of identifying the at least one third local energy minimum; $M_R$ is the number of local energy minima of the receptor used in the step of identifying the at least one second local energy minimum; $M_L$ is the number of local energy minima of the ligand used in the step of identifying the at least one first local energy minimum; $Z_{R,i}$ is the local configuration integral for the receptor near its local energy minimum i; $Z_{L,i}$ is the local configuration integral for the ligand near its local energy minimum i; $Z_{RL,i}$ is the local configuration integral for the complex near its local energy minimum i.

4. The method of claim 2, wherein at least one local configuration integral at an energy minimum is computed by the following steps:
    i. computing and diagonalizing a matrix of second derivatives of the energy at the energy minimum to obtain at least one eigenvector, each at least one eigenvector being associated with an eigenvalue;
    ii. computing the energies for molecular conformations generated by stepwise distortions away from an energy minimum along the at least one eigenvector and using the energies to evaluate a numerical configuration integral along the at least one eigenvector; and
    iii. defining for at least some of the at least one eigenvectors the Gaussian probability distribution based upon the corresponding eigenvalue and the temperature and evaluating the configuration integral along the eigenvectors by analytic integration of the Gaussian.

5. The method of claim 2, wherein the configuration integrals comprise integrals selected from the group consisting of: an integral of a Boltzmann factor, an integral of a Mayer factor or an integral of an Andersen factor.

6. The method of claim 1, wherein the first portion of the receptor is held rigidly fixed in a single conformation.

7. The method of claim 1, further comprising the step of:
    a. selecting a first and second portion of the ligand, wherein the first portion of said ligand is treated as restrained.

8. The method of claim 7, wherein the first portion of the ligand is held rigidly fixed in a single conformation.

9. The method of claim 1, wherein the first portion of the receptor is restrained by being held rigidly fixed in a single conformation.

10. The method of claim 1, wherein the first portion of the receptor is restrained by an added energy term which rises as the first portion of the receptor deviates from a specified conformation.

11. The method of claim 7, wherein the first portion of the ligand is restrained by an added energy term which rises as the first portion of the ligand deviates from a specified conformation.

12. The method of claim 10, wherein the added energy term varies quadratically with the deviation of the conformation of the first portion of the receptor from the specified conformation.

13. The method of claim 11, wherein the added energy term varies quadratically with the deviation of the conformation of the first portion of the ligand from the specified conformation.

14. The method of claim 1, wherein the first portion of the receptor is restrained to occupy only a selected set of energy minima.

15. The method of claim 7, wherein the first portion of the ligand is restrained to occupy only a selected set of energy minima.

16. The method of claim 1, wherein the first portion of the receptor is free to move as a unit.

17. The method of claim 7, wherein the first part of the ligand is free to move as a unit.

18. The method of claim 1, wherein the first and/or second portions of the receptor comprise multiple covalently disconnected segments of the receptor.

19. The method of claim 7, wherein the first and/or second portion of the ligand comprise multiple covalently disconnected segments of the ligand.

20. The method of claim 2, further comprising one or more of the following steps:
   a. adjusting with a fourth energy model the values of the first set of local configuration integrals computed in the step of computing a first set of local configuration integrals by recalculating the first energy model for a single conformation associated with each local energy minimum;
   b. adjusting with a fifth energy model the values of the second set of local configuration integrals computed in the step of computing a second set of local configuration integrals by recalculating the second energy model for a single conformation associated with each local energy minimum; and
   c. adjusting with a sixth energy model the values of the third set of local configuration integral computed in the step of computing a third set of local configuration integral by recalculating the third energy model for a single conformation associated with each local energy minimum.

21. The method of claim 2, wherein at least one local configuration integral for an energy minimum and its associated conformation is computed by approximating local energy variations around the associated conformation.

22. The method of claim 21, wherein the domain of the at least one local configuration integral is less than infinite in extent.

23. The method of claim 22, wherein the domain of the at least one local configuration integral at an energy minimum is determined by the steps of:
   i. computing and diagonalizing a matrix of second derivatives of the energy at the energy minimum to obtain at least one eigenvector, each at least one eigenvector being associated with an eigenvalue;
   ii. defining the Gaussian probability distribution based upon a corresponding eigenvalue and a temperature for each of the at least one eigenvectors; and
   iii. defining the integration range along each eigenvector as a multiple of the standard deviation of the corresponding Gaussian probability distribution.

24. The method of claim 20, wherein the first, second and third energy models use a first implicit solvation model and the fourth, fifth and sixth energy models use a second implicit solvation model, wherein the first and second implicit salvation models are different.

25. The method of claim 24, wherein the first, second and third energy models use a generalized Born solvation model and the fourth, fifth and sixth energy models use a numerical solution of the linearized or unlinearized Poisson-Boltzmann equation.

26. The method of claim 20, wherein the first, second and third energy models use an empirical force field and the fourth, fifth and sixth energy models use quantum mechanical electronic structure methods.

27. The method of claim 20, wherein the first, second and third energy models use a first empirical force field and the fourth, fifth and sixth energy models use a second empirical force field, wherein the first and second empirical force fields are different.

28. The method of claim 20, wherein the first, second and third energy models use an implicit solvent model and the fourth, fifth and sixth energy models are evaluated by thermodynamic integration or thermodynamic perturbation calculations of the solvation free energy.

29. The method of claim 1, wherein the ligand and the receptor, when complexed, are connected to each other by a covalent bond.

30. The method of claim 1, wherein internal coordinates of the ligand are specified in bond-angle-torsion coordinates.

31. The method of claim 1, wherein internal coordinates of the receptor are specified in bond-angle-torsion coordinates.

32. The method of claim 1, wherein internal coordinates of the ligand-receptor complex are specified in bond-angle-torsion coordinates.

33. The method of claim 1, wherein the position and orientation of the ligand relative to the receptor are defined by establishing a pseudo-bond joining one atom of the ligand to one atom of the receptor and using the pseudo-bond to define a pseudo-bond length, two pseudo-bond angles, and three pseudo-bond torsion angles.

34. The method of claim 1, wherein internal coordinates of the ligand are specified in Cartesian coordinates.

35. The method of claim 1, wherein internal coordinates of the receptor are specified in Cartesian coordinates.

36. The method of claim 1, wherein internal coordinates of the ligand-receptor complex are specified in Cartesian coordinates.

37. The method of claim 2, wherein the local configuration integrals of the first set are computed with the rigid rotor/harmonic oscillator approximation.

38. The method of claim 2, wherein the local configuration integrals of the second set are computed with the rigid rotor/harmonic oscillator approximation.

39. The method of claim 2, wherein the local configuration integrals of the third set are computed with the rigid rotor/harmonic oscillator approximation.

40. The method of claim 1, wherein the ligand is itself a multimolecular complex.

41. The method of claim 1, wherein the receptor is itself a multimolecular complex.

42. The method of claim 1, further comprising the step of:
   a. causing the ligand to bind with the receptor.

43. The method of claim 2, wherein the first set of local configuration integrals is computed using an unrestrained ligand.

44. The method of claim 2, wherein the second set of local configuration integrals is computed using an unrestrained receptor.

45. The method of claim 2, wherein the third set of local configuration integrals is computed using an unrestrained complex.

* * * * *

UNITED STATES PATENT AND TRADEMARK OFFICE
CERTIFICATE OF CORRECTION

| | | |
|---|---|---|
| PATENT NO. | : 8,140,268 B2 | Page 1 of 1 |
| APPLICATION NO. | : 11/695494 | |
| DATED | : March 20, 2012 | |
| INVENTOR(S) | : Michael Jason Potter et al. | |

It is certified that error appears in the above-identified patent and that said Letters Patent is hereby corrected as shown below:

Col. 25, Line 49-50, Claim 24, change "salvation" to --solvation--.

Signed and Sealed this
Twelfth Day of June, 2012

David J. Kappos
*Director of the United States Patent and Trademark Office*